United States Patent [19]
Miki et al.

[11] Patent Number: 5,595,895
[45] Date of Patent: Jan. 21, 1997

[54] EFFICIENT DIRECTIONAL GENETIC CLONING SYSTEM

[75] Inventors: Toru Miki, Rockville, Md.; Stuart A. Aaronson, Great Falls, Va.

[73] Assignee: The United States of America as represented by the Department of Health and Human Services, Washington, D.C.

[21] Appl. No.: 902,786

[22] Filed: Jun. 24, 1992

Related U.S. Application Data

[63] Continuation of Ser. No. 386,053, Jul. 28, 1989, abandoned.

[51] Int. Cl.$^6$ .......................... C12N 15/66; C12N 15/63; C12N 15/11
[52] U.S. Cl. .................... 435/172.3; 435/320.1; 536/23.1; 536/24.1; 536/24.2; 536/24.33
[58] Field of Search .................... 435/91, 172.1, 435/172.3, 320.1; 536/23.1, 24.1, 24.33, 24.2; 935/18, 19, 20, 21, 23, 24, 26, 27, 58

[56] References Cited

U.S. PATENT DOCUMENTS 5,001,230   3/1991   Brown et al. .......................... 536/23.5

OTHER PUBLICATIONS

Brooks (1987) in "Methods in Enzymology," (Academic Press, New York), vol. 152, pp. 113–129.
Groger et al., Directional Antisense and Sense Cloning Using Epstein–Barr Virus Episomal Expression Vectors, Gene, vol. 81, issued 1989, pp. 285–294.
Miki et al., An Efficient Directional Cloning System to Construct cDNA Libraries Containing Full–Length Inserts at High Frequency, Gene, vol. 83, issued Dec. 1989, pp. 137–146.
Finch et al., Human KGF is FGF–Related Effector of Epitrelial Cell Growth, Science, vol. 245, issued 18 Aug. 1989, pp. 752–755.
Palazzolo et al., A Family of Lambda Phage cDNA Cloning Vectors, . . . , Gene, vol. 52, issued 1987, pp. 197–206.
Zabarovsky et al., sK15–a Diphasmid for Construction Expression cDNA Libraries at . . . , Nucleic Acids Research, vol. 17, No. 11, issued May 1989, p. 4408.
Stengelin et al., Isolation of cDNAs for Two Distinct Human Fc Receptors . . . , The EMBO Journal, vol. 7, No. 4, 1988, pp. 1053–1059.
Han et al. *Nucl Acids Res* vol. 16 No. 24 Nov. 1988 p. 11837.
Han et al. *Nucl Acids Res.* vol. 15 No. 15 Jun. 1987 p. 6304.
Grimoldi et al. *Nucl Acids Res.* vol. 15 No. 22 Nov. 1987 p. 9608.
Swaroop et al., *Nucl Acids Res.* vol. 16 No. 17 1988 p. 8731.
Helfman et al. in Methods in Enzymology, vol. 152 1987 pp. 349–359 "Directional cDNA cloning in plasmid vectors by sequential addition of oligonucleotide linkers".
Aruffo et al. *Proc. Natl Acad. Sci* vol. 89 pp. 8573–8577 (1987).

*Primary Examiner*—Richard A. Schwartz
*Assistant Examiner*—Robert A. Hodges
*Attorney, Agent, or Firm*—Foley & Lardner

[57] ABSTRACT

A highly efficient genetic cloning system is disclosed which is particularly useful for cloning cDNA copies of eukaryotic mRNAs and can direct the orientation of inserts in λ-plasmid composite vectors with large cloning capacities. Cleavage of such vector DNA, by the restriction enzyme SfiI, for example, creates two different non-symmetrical 3' extensions at the ends of vector DNA. Using a linker-primer and an adaptor, cDNA is prepared to have two different sticky ends which can be ligated to those of the vector. When the cDNA fragments and the vector DNAs are mixed, both the molecules can assemble without self-circularization due to base-pairing specificity. This system provides (1) high cloning efficiency ($10^7$–$10^8$ clones/μg poly(A)$^+$ RNA), (2) low background (more than 90% of the clones contain inserts), (3) directional insertion of cDNA fragments into the vectors, (4) presence of a single insert in each clone, (5) accommodation of long inserts (up to 10 kb), (6) a mechanism for rescue of the plasmid part from a λ genome, and (7) a straightforward protocol for library preparation.

12 Claims, 5 Drawing Sheets

```
  1 GCCGGCCCCT CAGCCCTGCT GCCCAGCACG AGCCTGTGCT CGCCCTGCCC
 51 AACGCAGACA GCCAGACCCA GGGCGGCCCC TCTGGCGGCT CTGCTCCTCC
101 CGAAGGATGC TTGGGGAGTG AGGCGAAGCT GGGCGCTCCT CTCCCCTACA
151 GCAGCCCCCT TCCTCCATCC CTCTGTTCTC CTGAGCCTTC AGGAGCCTGC
201 ACCAGTCCTG CCTGTCCTTC TACTCAGCTG TTACCAACTC TGGGACCAGC
251 AGTCTTTCTG ATAACTGGGA GAGGGCAGTA AGGAGGACTT CCTGGAGGGG
301 GTGACTGTCC AGAGCCTGGA ACTGTGCCCA CACCAGAAGC CATCAGCAGC
351 AAGGACACCA TGCGGCTTCC GGGTGCGATG CCAGCTCTGG CCCTCAAAGG
```

FIG. 5(D)

```
  1 CCATTACTGT TGGAGCTACA GGGAGAGAAA CAGGAGGAGA CTGCAAGAGA
 51 TCATTTGGGA AGGCCGTGGG CACGCTCTTT ACTCCATGTG TGGGACATTC
101 ATTGCGGAAT AACATCGGAG GAGAAGTTTC CCAGAGCTAT GGGGACTTCC
```

EFFICIENT DIRECTIONAL GENETIC CLONING SYSTEM

This is a continuation of application Ser. No. 07/386,053, filed on Jul. 28, 1989, abandoned.

FIELD OF THE INVENTION

The present invention relates to vectors for molecular cloning of DNA segments, particularly to cloning vectors employing non-symmetrical restriction enzyme recognition sites for insertion of DNA segments in a defined direction relative to vector. This invention also relates to use of such vectors in methods for efficient cloning of genomic DNA segments and of complementary DNA (cDNA) copies of messenger RNA (mRNA) molecules from eukaryotic genes, and to the manufacture and use of novel products related to these vectors and methods.

BACKGROUND OF THE INVENTION

The development of DNA cloning techniques for complementary DNA (cDNA) copies of messenger RNA (mRNA) molecules has been of great value in the study of eukaryotic genes. In many cases, the amount of a given mRNA for which cDNA clones are desired is limited by the availability of appropriate tissue sources and/or a low concentration of that specific mRNA in those sources. Therefore, readily obtainable sources may provide only a few copies of a given mRNA molecule from which cDNA clones might be produced.

The requirements for any efficient method for cDNA cloning may be generally summarized as follows: first, full-length double-stranded cDNAs must be produced from the mRNA with high yield; the ends of the resulting DNA fragments must be made capable of being joined efficiently to the vector DNA by enzymatic ligation; production of undesirable ligation byproducts must be minimized; and, preferably, insertion of the cDNA into the vector DNA should provide expression of the cDNA to facilitate detection of the desired clone by means of the product.

Production of the protein product may be necessary for detecting a gene when no nucleic acid probes for the desired gene are available. More generally, such expression of the protein is desirable because, in terms of copy number, the protein provides a molecular signal that is greatly amplified in relation to the DNA molecules of the cloned gene inside the host cell.

As it is difficult to achieve high efficiency of conversion of mRNA molecules into full-length cDNA clones, especially when the mRNA of interest is relatively long, several refinements in cDNA cloning strategy have been made. Among them, the Okayama-Berg method significantly improved the efficiency of full-length cDNA cloning.

The Okayama-Berg approach has several advantages over previous, conventional methods for cloning cDNAs. The following section is intended to highlight these advantages in relation to the main steps of this complicated method. For a more complete and detailed description of the method, see the original publication [Okayama, H. and Berg, P. (1982) Mol. Cell. Biol. 2, 161–170], which is hereby incorporated herein by reference.

The main advantages of the Okayama-Berg method for cDNA clone relate to the fact that as part of the processing needed to form mRNAs, transcripts of eukaryotic genes undergo enzymatic addition of multiple adenosine residues at the 3' end, thereby acquiring what is known as a "poly(A) tail". In the present context, the term mRNA encompasses any RNA species from any source, natural or synthetic, having a 3' poly(A) tail comprising two or more adenosine residues.

In the original Okayama-Berg approach, synthesis of the first DNA strand from the mRNA template is initiated by annealing the 3' poly(A) of the eukaryotic mRNA to an oligo(dT) primer which forms an extension of one end of a DNA strand of the cloning plasmid. First strand cDNA synthesis by this "plasmid-priming" method directs the orientation of the sequence within the cDNA into a unique relationship with the sequence in the plasmid; hence, this approach has been called "directional" cloning. Directional cloning ensures that every cDNA clone that is formed will be correctly oriented for a promoter provided in the cloning plasmid (an SV40 promoter in the original Okayama-Berg system) to drive transcription of the proper cDNA strand to produce RNA with the correct sense for translation into the protein encoded by the original mRNA template.

To provide high efficiency of ligation in cloning DNA segments in general, restriction nucleases are utilized to produce short single-stranded ends on the DNA that are complementary in base sequence to any other DNA end produced by the same enzyme. Accordingly, these single-stranded ends can anneal together by forming specific DNA base pairs, or, in the vernacular, they are "sticky". This annealing greatly enhances the rate of joining DNA segments by enzymatic ligation and further provides a means for selectively joining ends of segments treated with the same enzyme.

In the original Okayama-Berg method, after synthesis of the first cDNA strand, an oligo(dG) tail is attached enzymatically to the free end of the plasmid-primed cDNA, and then the plasmid is cleaved by a restriction enzyme (HindIII) to produce a sticky end on the plasmid opposite to the end where the cDNA is attached. A short DNA fragment ("linker"), which contains the SV40 promoter and has a cleaved HindIII site on one end and oligo(dC) on the other, is then attached to the cDNA-plasmid molecule by ligation, to circularize the molecule.

In other, more conventional methods a (synthetic) linker may also be used to clone cDNAs, but it is attached after second strand DNA synthesis and further enzymatic repair which is necessary to form perfectly matched strands (i.e., a "flush" or "blunt" end). To protect internal restriction sites of the double-stranded cDNA from cleavage by the restriction enzyme required to allow ligation of the vector and linker, prior to addition of the linker, the cDNA is methylated with the appropriate DNA modification system associated with the given restriction enzyme. However, such protection may not be absolute; thus, internal sites may be cleaved at some frequency due to an incomplete methylation reaction. In contrast, in the original Okayama-Berg method, this problem of internal cleavage of cDNAs is obviated by cleavage of HindIII sites on the vector when the cDNA is represented as an RNA:DNA hybrid that resists restriction.

The Okayama-Berg approach provides yet another advantage over previous methods in which both ends of separately synthesized cDNAs are ligated to the vector ends at the same time, namely that according to Okayama-Berg, the necessary circularization of the vector DNA with the cDNA attached at one end is relatively efficient via the linker because only one juncture between the cDNA and vector molecules remains to undergo ligation.

Furthermore, the overall Okayama-Berg approach offers additional advantages over previous methods. Following circularization, a process called "RNA nick translation" using DNA polymerase I and RNase H is used which facilitates complete synthesis of the second strand along the entire first strand. This process overcomes the inherently low processivity of DNA polymerase I by using multiple sites for priming of second strand DNA synthesis with DNA primer fragments having random sequences.

Finally, since the Okayama-Berg vector has already been joined to the cDNA when the second strand is synthesized, truncation of cDNA molecules close to the 3' end of the cDNA generally does not occur, in contrast to other methods in which the second strand is completed while the 3' end of the first strand is free and, therefore, more susceptible to damage from nuclease activities.

Cloning vectors based on bacteriophage λ are also known. The second strand synthesis reaction of the Okayama-Berg method has also been utilized in a simpler cloning procedure [Gubler, U. and Hoffman, B. J. (1983) Gene 25, 253–269], allowing cDNA cloning in such λ vectors [Huynh, T. V., Young, R. A. and Davis, R. W. (1985) in DNA Cloning, A Practical Approach, ed. Glover, D. (IRL, Oxford), Vol. I, pp. 49–78]. This λ-based cDNA cloning method has been widely used, mainly due to the high efficiency of transmission of recombinant DNA into cells by means of infectious phage particles, which are produced with in vitro DNA "packaging" systems. λ phage cloning systems also offer convenient clone screening capabilities due to tolerance of a high density of λ plaques on test plates to be screened, compared with most plasmid systems which permit only lower densities of bacterial host colonies.

Early λ systems for cDNA cloning, however, while retaining the second strand synthesis strategy of the original Okayama-Berg plasmid method, lack some of its other advantages. For example, directional cloning is not possible in those original λ systems. In addition, multiple inserts and truncated cDNAs are frequently obtained. Further, despite the high packaging efficiency for native λ DNA molecules, the packaging efficiency of recombinant DNA molecules that are produced by cleavage of intact linear λ molecules and ligation with cDNA fragments is usually low compared to that of intact λ DNA.

Recently, directional cloning capabilities have been introduced into various λ vectors. For example, one such directional λ vector employs a site for insertion of DNA segments that comprises two different restriction enzyme cleavage sites [Meissner, P. S., et al. (1987) Proc. Nat. Acad. Sci. USA, 84, 4171–4175]. The cDNA molecules are primed with oligo(dT), made double-stranded, and then methylated with the enzymes needed for protection against internal cleavage by both of the nucleases used in the DNA insertion site of the vector. A linker segment containing a cleavage site for only one of the nucleases of the insertion site is added to both ends of the cDNA. The combination of the last two A:T base pairs on the 3' end of the cDNA with the sequences at one end of the linker, however, creates a cut site for the other of the two nucleases of the insertion site. Thus, after restriction with both nucleases of the insertion site, the individual cDNA segments can ligate into the vector only in a single direction with respect to the two different cleavage sites in the vector.

Various general disadvantages of this particular approach for cDNA cloning in λ phage, compared to the Okayama-Berg plasmid method, have been described above in relation to other systems; and other problems specific to this approach have been noted [Meissner, P. S., et al. (1987), supra]. Nevertheless, it was reported that one cDNA library constructed by this method, starting from 5 µg of mRNA, contained about $2 \times 10^8$ clones with 8 of 10 having cDNA inserts (i.e., the reported cloning efficiency was about $3 \times 10^7$ recombinants per µg of poly(A)+RNA).

Directional cloning in other λ phage vectors has also been reported [Palazzolo, M. J. and Meyerowitz, E. M. (1987) Gene 52, 197–206]. [These vectors are known as λSWAJ or λGEM, certain variants of which (LambdaGEM™2 and LambdaGEM™4) are commercially available from Promega Corporation of Madison, Wis. The λGEM type of vectors are also examples of a composite vector comprising both a λ phage genome and an embedded plasmid (GEM)]. The directional cloning scheme in these λ vectors utilizes two different restriction enzyme cleavage sites at the site for insertion of DNA. Thus, for example, to attach the end of a cDNA corresponding to the poly (A) end of the mRNA to a particular end of the cleaved vector DNA that has a sticky end for the restriction enzyme SacI, a synthetic DNA "linker-primer" segment is used which combines a single-stranded oligo(dT) primer with a restriction site for the enzyme SacI. After second strand synthesis, a linker segment with the site of a second restriction enzyme is ligated to the other end of the cDNA, which is then restricted with both enzymes of the insertion site of the vector, according to much the same strategy as described for the previous example of a directional λ phage vector.

This particular approach for directional cloning in a λ vector, however, cannot be used to obtain full-length cDNAs of certain mRNAs because it requires cleavage of the cDNA molecules by the restriction enzyme SacI and a second enzyme (e.g., XbaI) without first protecting the internal sites for these enzymes by appropriate methylation. [In an alternative version of the scheme reported by Palazzolo and Meyerowitz, supra, the XbaI enzyme was replaced by EcoRI and the cDNA was methylated to protect against only this one enzyme.]Sites for these particular enzymes occur frequently by chance in natural nucleotide sequences. Thus, restriction of cDNAs with enzymes like these, as taught in this approach, causes truncation of cDNA inserts with internal SacI (and/or XbaI) sites. In relation to cloning efficiency, it may be noted that this publication described a single cDNA library constructed by this method, starting from 1 µg of poly(A)+ RNA, that contained about $1.6 \times 10^6$ clones with cDNA inserts. In addition to the publications on directional cloning systems described above, there is a report which describes a non-directional plasmid-based system that uses an efficient oligonucleotide-based strategy to promote cDNA insertion into the vector [Aruffo, A. and Seed, B. (1987) Proc. Nat. Acad. Sci. USA 84, 8573–8577]. This method uses synthetic DNA adaptors that encode a recognition site for a particular restriction enzyme, BstXI, which has a variable recognition sequence, as illustrated below:

where A, T, G and C indicate nucleotides having the DNA bases adenine, thymine, guanine, and cytosine, respectively (for which the pairs A:T and G:C are complementary), and N and N represent bases that are included within the recognition site sequence but that can be any of the usual DNA bases, provided only, of course, that each N and the corresponding N on the opposite DNA strand be complementary. The arrows (↓ and ↑) indicate the cleavage sites on the upper and lower DNA strands, respectively. Accordingly, cleavage of the BstXI site creates a 4-base single-stranded extension (sticky end) on the 3' end that varies from site to site.

The report above discloses a plasmid vector with a site for insertion of DNA segments in which two identical BstXI sites were placed in inverted orientation with respect to each other and were separated by a short replaceable segment of DNA. Inversion of a DNA sequence consists of representing the base sequence of each strand, conventionally expressed in the 5' to 3' direction of the polynucleotide backbone, in a DNA strand with the same base sequence presented in the 3' to 5' direction (e.g., inversion of the DNA sequence 5'-ACTG-3' produces the DNA sequence 3'-ACTG-5' or, in the conventional 5' to 3' format, 5'-GTCA-3'.

With the particular BstXI recognition sequence that was employed in this vector, the 4-base single-stranded ends of the inverted sites created on the two ends of the vector DNA by restriction with the BstXI enzyme were not able to anneal with one another. This situation is illustrated below, where two identical sites, one inverted relative to the other and separated by an unspecified sequence (N . . . N), are shown; the sticky ends of the vector produced by cleavage with the BstXI enzyme are shown in bold print:

(Note that the reference does not specify the entire BstXI recognition sequence that was used; only the sequence of the sticky end is clearly defined, as indicated below by inclusion of the N symbol where necessary).

Inspection of these single-stranded end sequences on this plasmid vector reveals that they are identical, due to the inversion of one of the sites relative to the other. Thus, the ends of the vector with inverted and non-inverted copies of this particular BstXI restriction site sequence cannot anneal with each other. Similarly, the restricted ends of the spacer DNA segment between these two sites will be identical. Accordingly, to clone cDNA segments in this vector, a synthetic adaptor was attached to each end at the double-stranded stage, by blunt end ligation, giving them the same termini as the replaceable segment that was removed from the vector with BstXI. The specific adaptor used in the above report comprises the following oligonucleotide sequences:

5'-CTTTAGAGCACA-3'

3'-GAAATCTC -5'.

Obviously, addition of this single adaptor to both ends of the cDNA segments would provide those segments with ends (in bold type) that could anneal and subsequently ligate efficiently to both identical vector ends.

Thus, Aruffo and Seed, 1987, supra, discloses a method using this particular BstXI recognition site sequence, whereby neither the cDNA (with attached adaptors) nor the isolated vector DNA (after being freed from the replaceable segment after cleavage with BstXI) was able to ligate to itself. This work, however, neither teaches nor suggests general requirements for a BstXI recognition sequence, or for those of other restriction enzymes, to be usable in this cloning approach.

Further, as these workers pointed out, their strategy did not provide a directional cloning capability. After first alleging that such directional capability was not needed, they admitted that, nonetheless, they had devoted considerable unsuccessful efforts to developing an alternative means of producing mRNA from every cDNA clone, namely a bidirectional transcription capability whereby both strands of an inserted cDNA would be transcribed. They concluded that this goal cannot be easily attained, at least not in their cloning host system. The authors stated, moreover, that they could obtain cloning efficiencies with their plasmid that were between 0.5 and $2\times10^6$ recombinants per µg of mRNA, which were said to compare favorably with those described for certain cloning systems based on phage λ. In the only example of a cDNA library described in this reference, however, the yield of cDNA clones obtained by this method was actually stated to be only $\approx 3\times10^5$ recombinants from 0.8 µg poly (A) -containing RNA (i.e., less than $0.4\times10^6$ recombinants per µg poly(A)-containing RNA).

Thus, there has been a continuing need for methods and vectors which would provide a higher yield of cDNA clones from limited amounts of eukaryotic mRNAs while also providing an improved means of directing orientation of inserted cDNA fragments within vector DNAs.

SUMMARY OF THE INVENTION

The present invention contemplates the application of methods of recombinant DNA technology to fulfill the above needs for increased efficiencies in DNA cloning systems and, in particular, to develop new means for directional insertion of cDNA fragments into cloning vectors.

More specifically, it is an object of the present invention to provide means for directing assembly of insert DNAs into vector DNAs to form a unique, predetermined recombinant structure having the desired number and orientation of each needed DNA fragment, so that the number of resulting clones containing single inserts, as well as the probability of obtaining a full-length clone from each mRNA molecule, are enhanced.

Further, it is an object of this invention to provide a cDNA cloning system which combines the features of this highly efficient cloning strategy with advantageous features of λ phage vectors to overcome limitations of the presently available λ cloning systems.

Accordingly, the present invention relates to highly efficient means for inserting DNA segments into cloning vectors in a defined orientation, and a method for using such means that is referred to herein as the "automatic directional cloning (ADC)" method. Novel DNA vectors and DNA segments are also included.

Appreciation of the operation and advantages of this invention requires further analysis of the problems in the prior approaches. The understanding of these problems by the present inventors lead to development of this invention.

The present invention has been developed in light of recognition by these inventors of major sources of the limitations on cloning efficiency with the present systems designed for directional cloning, that they all employ restriction enzymes with recognition site sequences having one or both of the following disadvantages: they are either too short or they have a particular type of symmetry called "dyad" symmetry.

As noted above, present λ phage vectors for directional cloning of cDNAs suffer inefficiencies due in part to their use of restriction enzymes with recognition sequences that occur frequently in natural DNA sequences. Some problems relating to this issue might be solved by choosing a restriction enzyme with an infrequently occurring site (i.e., a longer recognition sequence which, by chance, would occur less frequently in random natural DNA sequences).

However, even when modified to utilize an infrequently cutting restriction enzyme, the present implementations of directional cloning in λ have a drawback that is common to any cloning scheme using restriction enzymes with recognition sequences having dyad symmetry of the sticky ends produced by cleavage with the enzyme.

Typical restriction enzymes with recognition site sequences having dyad symmetry make staggered cuts in the two opposing DNA strands at symmetrical points surrounding the center of a dyad pattern. Cleavage by this type of enzyme produces short single-stranded ends which are complementary in base sequence to those of any other DNA fragment produced by cleavage with the same enzyme.

For example, the recognition site of the commonly used restriction enzyme, EcoRI, consists of the following complementary sequences which when cleaved by the enzyme, produce the 4-base extension of the 5' end of the DNA containing the dyad "TTAA" (shown in bold face type):

5'-GAATTC-3'
3'-CTTAAG-5' where A, T, G and C indicate DNA bases, as described above for the BstXI site. Inspection of this EcoRI sticky end sequence readily reveals that inversion of this sequence produces its complement, namely "AATT". Thus, any DNA end produced by EcoRI can anneal to any other such DNA end; and, therefore, any EcoRI sticky end can also be ligated efficiently to any other such end. Similarly, all DNA ends which are produced by any one restriction enzyme that generates sticky ends characterized by dyad symmetry are in the case of each sticky end sequence readily ligatable one to another. [Hereinafter, such "self-ligatable" single-stranded ends of DNA that are producible by a restriction enzyme will be simply referred to as "symmetrical ends", and the enzymes that produce them, as "symmetrical restriction enzymes".]

In light of this symmetrical nature of many restriction enzyme recognition sites, one of the major problems with existing directional λ vectors can be more fully appreciated. When the two end fragments of cleaved λ DNA (i.e., the so-called λ "arms") are ligated with cDNA fragments, several products are produced, only some of which constitute the desired infectious DNA molecules containing cDNA inserts. For instance, consider the simplest case, when the ends on both the cDNA and on each of the "left" and "right" λ arms (as the two λ DNA arms have been designated in a genetic mapping convention) have been cut by the same symmetrical restriction enzyme. Here, linear structures other than those with the desired order (i.e., "left arm-cDNA insert-right arm") may form in significant amounts during ligation with cDNA fragments; and the cDNAs trapped in these other, nonviable structures cannot produce phage clones. These undesirable ligation byproducts may include self-ligation products of the two ends of individual vector or cDNA segments, consisting of circular DNAs. Ligation products in this instance may also comprise vector-cDNA combinations containing multiple inserts, which, even if viable, may create problems in expression or identification of original mRNA structure.

On the other hand, when each end of the vector and insert cDNA molecule are ultimately produced by two different symmetrical restriction enzymes, as in the present directional λ systems, these ends are then physically distinguishable in relation to the polarity of the encoded genetic information in each DNA segment, i.e., the matching of complementary sticky ends on vector DNAs and cDNAs results in the desired directional cloning of the cDNA insert relative to functional sequences in the vector (e.g., a promoter). Further, circularization due to self-ligation of cDNAs or vectors without inserts is eliminated by the use of two different symmetrical restriction enzymes.

Other undesirable ligation byproducts remain, however, in the usual two enzyme approach for directional cloning using symmetrical enzymes. Some of these are dimers of vector or cDNAs, which may be designated, for example, as "tail-to-tail" or "head-to-head" dimers. Thus, even when vector and cDNAs are made by cutting with two different symmetrical enzymes, head-to-head and tail-to-tail dimers are not eliminated, although the population of desired molecules is significantly higher.

In contrast to existing systems based on λ phage, the automatic directional cloning method does not permit cDNA or vector fragments to ligate to each other, ensuring the presence of a single insert in each clone, as well as higher cloning efficiencies and lower backgrounds of clones that do not contain cDNA inserts.

To accomplish these goals, the present invention contemplates use of restriction enzymes which produce single-stranded ends that do not exhibit dyad symmetry (hereinafter referred to as "non-symmetrical ends" and correspondingly, non-symmetrical recognition site sequences and enzymes). Although certain preferred embodiments of the present invention employ derivatives of bacteriophage λ as the vector, which further comprise embedded plasmid genomes, this invention can be practiced with any self-replicating DNA molecule (i.e., a "replicon") serving as the vector for DNA cloning in any host in which the selected replicon can be replicated.

Work cited in the Background above describes a plasmid-based system that advantageously employs two identical BstXI recognition site sequences, albeit in two different orientations. This single recognition sequence is non-symmetrical according to the definition in the present disclosure, although the reference does not describe the BstXI sequence in such terms or otherwise characterize this sequence as such. The present invention is clearly distinguishable from this previous approach, as described below.

Use of BstXI sites is not readily applicable to the λ system, due to the existence of multiple BstXI recognition sites in the λ phage genome, owing to the number of base pairs in the variable recognition sequence that are not allowed to vary (i.e., the "invariable base pairs" being only six).

Accordingly, in one aspect the present invention relates to a genetic cloning vector comprising at least one replicon, and a site for inserting DNA segments to be cloned that includes at least two non-symmetrical restriction enzyme recognition sequences that are identical, where the first of these identical recognition sequences is in the inverted orientation with respect to a second identical sequence; and, in addition, the identical restriction enzyme recognition sequences include greater than six positions having invariable DNA base pairs. Recognition site sequences of the enzyme SfiI, for example, fulfill both the length and asymmetry requirements for this aspect of the invention, as will become evident below.

On the other hand, in plasmid systems or other replicons lacking BstXI sites, either naturally or due to genetic engineering, two BstXI site sequences that are in the same instance non-symmetrical and nonidentical can be advantageously employed for efficient cloning of DNA segments according to the present invention.

More generally, this aspect of this invention may be practiced with any two non-symmetrical restriction enzyme recognition sequences that are not identical (recognitions site sequences of the enzyme SfiI, for instance).

Accordingly, the present invention also relates to a genetic cloning vector comprising at least one replicon, and a site for inserting DNA segments to be cloned that includes at least two non-symmetrical restriction enzyme recognition sequences that are nonidentical. In this aspect of the invention, two of the non-symmetrical restriction enzyme recognition sequences can be selected advantageously to be cleavable by a single restriction enzyme, for example, BstXI or, alternatively, SfiI; or each of two nonidentical restriction enzyme recognition site sequences may be selected to be cleavable by a different enzyme. Preferably, at least one of the non-symmetrical recognition sequences includes greater than six positions having invariable DNA base pairs; and most preferably, two nonidentical recognition sequences include greater than six positions having invariable DNA base pairs, as typified by SfiI recognition site sequences.

The present invention further relates to a vector, as described above, in which the replicon comprises a form of bacteriophage λ.

The vector may advantageously further comprise regulatory elements located in relation to the site for insertion of DNA segments such that, when a DNA segment is inserted into this site, at least a portion of the sequences of the DNA segment is transcribed. This portion may be derived from either one of the strands of the inserted double-stranded DNA segment, or from both of these strands.

In one major embodiment of this aspect of this invention, these regulatory elements in the vector consist of promoters that entirely originate from bacteriophage. By the phrase "originate from" it is meant that the regulatory element (e.g., promoter) is encoded in the genome of the instant organism or virus (e.g., bacteriophage) as it occurs in nature. It should be noted here that it is well known that, generally, promoters that originate from bacteriophage are not able to initiate transcription in eukaryotic hosts. This particular embodiment of the present invention is exemplified by two λ-plasmid composite vectors, LambdaGEM™11 and LambdaGEM™12, which are commercially available from Promega Corporation of Madison, Wis.

According to available information at the time of the present disclosure, these particular LambdaGEM™ vectors apparently were first disclosed in the 1988/1989 Catalogue and Applications Guide for Biological Research Products published and distributed by Promega Corporation in August of 1988, the entirety of which is hereby incorporated herein by reference. The following excerpts of that catalog describe these particular vectors and some of their various uses, particularly those relating to transcription from bacteriophage promoters.

Section 11, page 5:

The LambdaGEM-11 vector is a multi-functional genomic cloning vector designed for high resolution mapping of recombinant inserts, simplified genomic library construction, ultra-low background of non-recombinants, and rapid genomic walking. This lambda replacement-type cloning vehicle contains the following features (FIG. 2 [not shown]): dual opposed bacteriophage T7 and SP6 RNA polymerase promoters, flanking asymmetric SfiI restriction sites, and a multiple cloning site with strategically positioned XhoI and BamHI restriction sites. The LambdaGEM-11 vector also contains unique sites for SacI, AvrII, EcoRI, and XbaI. Because it is a derivative of EMBL3 (1), DNA fragments ranging from 9–23 kb can be cloned in the LambdaGEM-11 vector and the Spi phenotypic selection against non-recombinants is available. The vector was designed to make use of the SfiI recognition sites flanking the promoters for the high resolution restriction mapping of insert DNA using the Sfi linker mapping system (Sec. 11, pg. 8).

The T7/SP6 phage promoters simplify chromosomal "walking", as RNA probes synthesized from the extremities of the cloned insert can be used to search a library for overlapping sequences in either direction. In addition, the nucleotide sequence of the end of an insert cloned in the LambdaGEM-11 vector can be obtained directly form the phage template by hybridizing an SP6 or T7 oligonucleotide primer, followed by a chain termination sequencing reaction (2,3).

Two cloning strategies for genomic library construction, using DNA partially digested with MboI or Sau3AI, are available with the LambdaGEM-11 dephosphorylated BamHI arms. A new cloning strategy (4) relies on the exclusive specificity with which partially filled-in XhoI LambdaGEM-11 arms (XhoI half-site arms) can be combined with partially filled-in Sau3AI digested genomic DNA. The only ligation products possible are single copies of genomic inserts with appropriate arms, since the partial fill-in prevents self-ligation reactions of vector arms, central stuffer, and genomic fragments. This method also makes genomic DNA fractionation unnecessary, is very rapid (FIG. 3 [not shown]), and requires small amounts of starting material. The XhoI and BamHI sites in the LambdaGEM-11 vector are strategically positioned 6 and 11 bases, respectively, from the transcription initiation site of either promoter.

AS measured by in vitro packaging, recombinant efficiencies of $3 \times 10^7$ pfu/g DNA have been achieved using a test insert ligated to LambdaGEM-11 dephosphorylated BamHI or XhoI half-site arms using Packagene® lambda packaging extracts. The background for self-ligated arms alone is typically <100 pfu/μg DNA in either case. This ultra-low background level of non-recombinant vector DNA has three important advantages: it eliminates the need for the Spi genetic selection against the parental vector, which is known to result in biased libraries (5), non-productive ligation events are minimal, thereby resulting in larger genomic libraries, and fewer filters need be processed for screening a library. For detailed protocols describing the use of this vector, see Sec. 11, pg. 12.

Section 11, page 6:

The LambdaGEM-12 vector is a multi-functional genomic cloning vector designed for high resolution restriction mapping of recombinant inserts, simplified genomic library construction, ultra-low background of non-recombinants, and rapid genomic walking. This lambda replacement-type cloning vehicle contains the following features (FIG. 4 [not shown]): dual opposed bacteriophage T7 and SP6 RNA polymerase promoters, RNA polymerase promoters [sic], flanking asymmetric SfiI restriction sites, and a multiple cloning site with strategically positioned NotI and BamHI restriction sites. The LambdaGEM-12 vector also contains unique sites for SacI, EcoRI, XhoI, and XbaI. Because it is a derivative of EMBL3(1), DNA fragments ranging from 9–23 kb can be cloned in the LambdaGEM-12 vector and the phenotypic selection against non-recombinants is available.

Accordingly, the present invention relates to a vector that is either LambdaGEM™11 or LambdaGEM™12. Further details of the use of these vectors for restriction mapping of inserted DNA segments, according to the SfiI Linker Mapping System mentioned above, are extracted from the Promega catalog below.
Section 11, page 8:

The multi-functional LambdaGEM™-11 and LambdaGEM™-12 genomic cloning vectors have been engineered specifically for high resolution restriction mapping of recombinant inserts. The vectors, derivatives of EMBL3, possess SfiI restriction sites flanking bacteriophage T7/SP6 RNA polymerase promoters and a multiple cloning region (Sec. 11, pg. 5). The flanking SfiI restriction sites allow most inserts to be excised as a single fragment, since this 8-base recognition sequence occurs infrequently in genomic DNA (in theory, once every 65,536 bp).

SfiI recognizes the interrupted palindrome GGCCNNNN/NGGCC and cleaves within the central unspecified sequence, leaving a 3-base 3' overhang. The nucleotide sequence of the central region which becomes the overhanging termini thus may contain any of the four possible bases. The flanking SfiI sites in the vectors have been designed in an asymmetric fashion, so that the site on the left is distinct from the site on the right. Therefore, radiolabeled linkers complementary to either the left or right SfiI termini can be ligated separately to the SfiI excised genomic DNA. Once the insert has been asymmetrically labeled, a high resolution restriction map can be determined by partial digestion with a frequent cutting restriction endonuclease such as Sau3AI followed by gel electrophoresis and autoradiography (FIG. 6 [not shown]).

The mapping resolution of this method is an order of magnitude greater than conventional cos site oligo labeling, since only the ends of the centrally located insert are labeled instead of the ends of the 20 kb and 9 kb arms of the vector. The variable results generated from inaccurate size estimates of large restriction size fragments, as well as anomalous bands which result from the fusion of the insert with a vector fragment, are eliminated with this system. For a detailed protocol describing the use of this system, see Sec. 11, pg. 14.

Figure 1A:
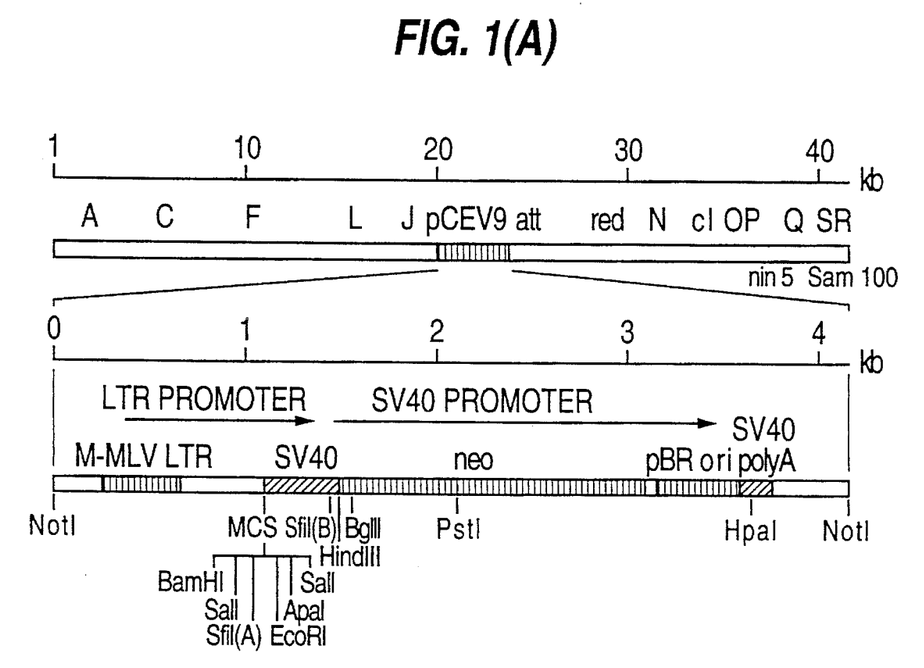
Figure 1B:
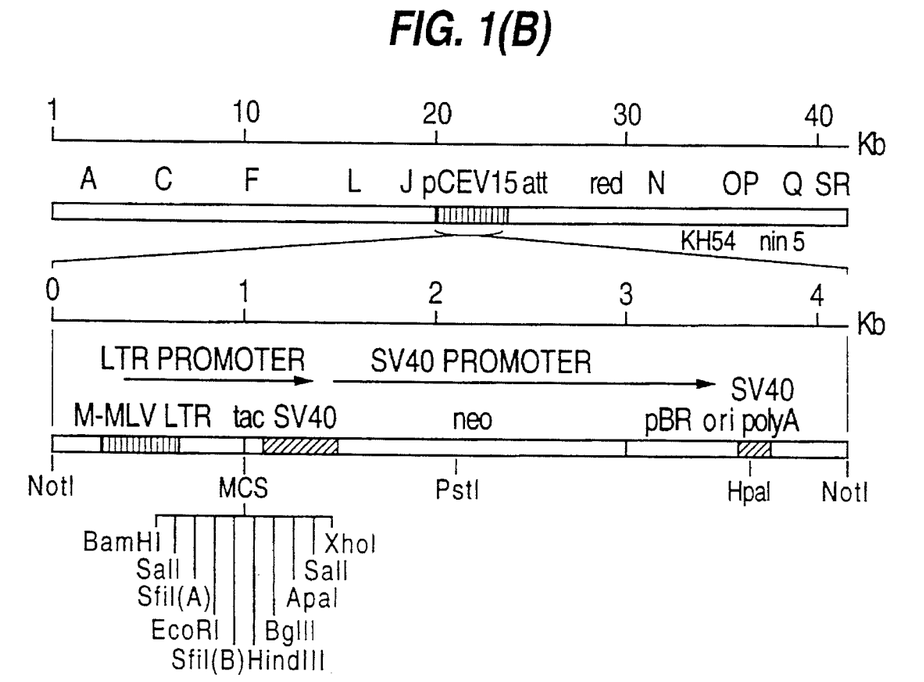

Still further, the present invention relates to a vector having nonidentical non-symmetrical restriction enzyme recognition site sequences, as described above, also including regulatory elements located such that the sequences of an inserted DNA segment are transcribed, as in the LambdaGEM™ vectors above, but where the regulatory elements are at least partly of eukaryotic origin. A principal embodiment of this aspect of the present invention is exemplified by two λ-plasmid composite vectors, λpCEV15 and λpCEV9, the structures of which are depicted in FIG. 1 and described further below.

In cloning operations with these two vectors, a DNA segment, a cDNA, for example, is cloned between two SfiI sites, A and B, as described in the section below relating to the automatic directional cloning method. The vectors are designed as eukaryotic expression vectors, utilizing the M-MLV LTR promoter, and they contain the SV40 early promoter-driven neo gene as a selectable marker.

Thus, the present invention further relates to a genetic cloning vector comprising at least one replicon, and a site for inserting DNA segments to be cloned that includes at least two nonidentical restriction enzyme recognition sequences that are non-symmetrical, where the vector also includes a selectable marker that is functional in eukaryotic cells in which the vector can be replicated. The term "functional" as used here means that the gene for the marker is expressed and that a selection scheme for that marker is operable in these eukaryotic cells.

In these two particular exemplary vectors, the form of λ-plasmid composite vector was chosen to take advantage of the efficient packaging and high density screening in λ systems, and simpler DNA preparation and analysis in plasmid systems. After isolation of clones of interest, pCEV plasmids with cDNA inserts can be obtained by NotI digestion of crude λ DNA preparations and ligation followed by transformation of bacterial cells. The λ genotype which supports healthy growth (red$^+$, gam$^+$) was chosen to maintain the intactness of inserts during the amplification step of the libraries. Deletion and/or insertion derivatives generated during the amplification step, if any, would not accumulate in the population, since they would not have a growth advantage.

λpCEV15 has several advantages over λpCEV9 as follows: (1) λpCEV15 does not require the supF mutation in host cell due to the S+ allele in the λ genome. (2) λpCEV15 does not lysogenize host strains due to the deletion of the cI gene. (3) cDNA inserts in λpCEV15 can be cut out by SalI digestion. (4) λpCEV9 loses the functional SV40 promoter after the cDNA insert is cloned, while λpCEV15 does not. (5) λpCEV15 can accommodate longer cDNA inserts (up to 10.5 kb) than λpCEV9 (up to 8.5 kb). (6))λpCEV15 DNA contains a unique HindIII site.

λpCEV9 has at least two advantages over λpCEV15. The λpCEV9 genome has a stuffer fragment between the two SfiI sites, which would be replaced by cDNA inserts during cloning process. Generally, it has been found that λpCEV9 cDNA libraries have lower backgrounds than λpCEV15 libraries, presumably because the presence of the stuffer fragment in λpCEV9 separates the two SfiI sites enough to ensure complete SfiI cleavage. It has also been observed that λpCEV9 grows more stably without accumulation of fast-growing derivatives. This is likely due to the longer size of the genome compared to that of λpCEV15.

In another aspect, the present invention relates to a method for cloning of DNA segments referred to as the automatic directional cloning method. In particular, the present invention relates to a method for cloning a cDNA copy of a eukaryotic mRNA, comprising the following steps (which are further illustrated in FIG. 3 and in the Description of Specific Embodiments, below):

(i) annealing a linker-primer DNA segment comprising a single-stranded oligonucleotide which has oligo(dT) at the 3' end, and a single-stranded extension at the 5' end that is included in a first non-symmetrical restriction enzyme recognition sequence.

[Note that this first recognition sequence is identical to one of two non-symmetrical sites in the vector that are used for direction cDNA cloning.]

(ii) enzymatically synthesizing the first strand of the cDNA from the linker-primer that is annealed with the mRNA molecule;

[Typically, this may be accomplished using a reverse transcriptase. During the first strand synthesis reactions, the single-stranded linker-primer is repaired so as to be double-stranded. Thus, the single-stranded extension referred to in this method may be present as such in the linker-primer, or it may be produced from a double-stranded region of linker-primer by cleavage with a restriction enzyme following ligation of the linker-primer to the cDNA.]

(iii) enzymatically synthesizing the second strand of the cDNA using the first strand as the template under conditions such that single-stranded extensions on the synthesized cDNA molecule are made double-stranded;

[Typically, the second strand is synthesized by DNA polymerase I from the nicks on the RNA moiety introduced by RNase H associated with the reverse transcriptase. The linker-primer is converted to the double-stranded form in the first or second strand synthesis step. T4 DNA polymerase treatment makes double-stranded any single-stranded extensions remaining on the synthesized cDNA molecule.]

(iv) ligating onto the blunt-ended cDNA resulting from synthesizing the second strand, an adaptor DNA segment comprising a second non-symmetrical restriction enzyme recognition sequence that is nonidentical to the first non-symmetrical restriction enzyme recognition sequence;

[In the case of a principal embodiment of this aspect of the invention, ligation of the adaptor ligation directly adds one single-stranded extension to the cDNA molecule. Alternatively, however, this extension could be exposed by cleavage of the recognition site on a double-stranded portion of the adaptor after ligation to the cDNA.]

(v) exposing the cDNA resulting from ligation with the adaptor to one or more restriction enzymes that can cleave the first and second non-symmetrical restriction enzyme recognition sequences under conditions such that both of these sequences are cleaved, resulting in the vector DNA having two single-stranded ends that are not complementary;

[This restriction causes exposure of at least one of the single-stranded extensions needed on the cDNA by cleavage of the recognition site on the repaired linker-primer portion of the cDNA molecule. If the non-symmetrical site in the adaptor is also uncleaved at this point, it may also be restricted at this step. In a principal embodiment, a single enzyme can cleave the non-symmetrical sites on both the linker-primer and the adaptor; but in other embodiments, two different enzymes may be required.]

(vi) ligating the cDNA resulting from cleavage with the enzymes to DNA of a genetic cloning vector, where the vector comprises
  at least one replicon; and
  a site for inserting DNA segments to be cloned that includes at least two non-symmetrical restriction enzyme recognition sequences,
  and where in the vector DNA, at least two non-symmetrical restriction enzyme recognition sequences have been cleaved by one or more enzymes that can cleave those recognition sequences, resulting in vector DNA having two single-stranded ends that are not complementary; wherein further,

[Thus, the two ends of the cleaved vector DNA cannot anneal and be ligated together. Cleavage of the vector DNA at both non-symmetrical sites usually releases a short DNA segment from between the, the "stuffer"; for the highest yield of clones containing cDNA inserts, this stuffer is removed from the cleaved vector DNA prior to ligation of the vector with cDNA.]

one of the single-stranded ends on the cleaved vector DNA has a sequence that is complementary to the single-stranded extension on the linker-primer attached to the cDNA; and the other single-stranded end on the cleaved vector DNA has a sequence that is complementary to the single-stranded extension on the adaptor attached to the cDNA; and

[Thus the cDNA cannot circularize and is attached to the vector in a specific direction.]

(vii) transforming a suitable host cell with the recombinant DNA segment comprising the cDNA and the vector DNA that results from the ligation of cDNA to vector DNA; and

[Various genetic transformation methods known in the art may be used. In a principal embodiment, the vector is a form of bacteriophage λ and, therefore, the recombinant DNA containing cDNA inserts is packaged in vitro into phage particles which are then used to infect a bacterial host cell. Alternatively, for example, $CaCl_2$ precipitation of DNA may be used to transform host cells, especially mammalian cells.]

(viii) identifying a clone of host cells, resulting from transformation with said recombinant DNA, that contains a recombinant DNA segment including said cDNA.

[Various strategies well known in the art of genetic engineering may be used to identify a clone of the desired cDNA, including hybridization with nucleic acid probes, immunological detection of expressed antigens, and assays for functional products, to name but a few.]

The strategy underlying this cDNA cloning method of the present invention is based on the following theory, explained in terms of particular examples of a principal embodiment, which is presented to aid in understanding the method and does not in any way limit the scope of the invention as defined by the appended claims.

When vector and insert DNA fragments are mixed and ligated in a typical cloning experiment, several molecules are produced in addition to those desired. These include self-ligation products of vectors or inserts, head-to-tail or head-to-head dimers of vector or insert, and vector DNA containing multiple inserts. Formation of these molecules would reduce the cloning efficiency. Even when vector and insert DNAs are made by cutting with two different enzymes, formation of ligation products such as head-to-head dimers can not be eliminated, although the population of desired molecules is significantly higher and insertion occurs in a defined orientation.

Figure 2A:
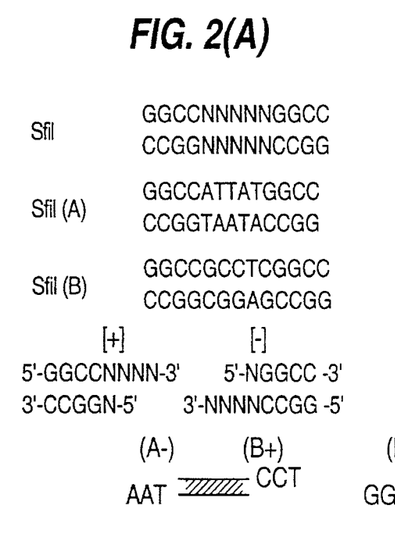
FIG. 2A, FIG. 2B and FIG. 2C. Scheme of the automatic directional cloning system. Panel (A), Nucleotide sequences of the SfiI sites. The general structure of the SfiI site is shown at the top, where the letter N denotes any nucleotide. The two SfiI sites specific to the vectors, SfiI (A) and SfiI (B), are shown under the general structure. The upper strands are shown in the 5' to 3' direction, while the lower ones are in the opposite direction. The bottom of the figure shows the sequences of the ends produced by the SfiI cleavage of the general SfiI site. The left and right half sites are denoted as SfiI ($^+$) and SfiI ($^-$), respectively. Similarly, the sequences of SfiI (A$^+$), SfiI (A$^-$), SfiI (B$^+$), and SfiI (B$^-$) half sites can be derived from the sequences of the SfiI (A) and SfiI (B) sites. Panel (B), preparation of the λpCEV vector arms. λpCEV vector DNA is shown at the top, where cosL and cosR represent the left and right cohesive ends of λ, respectively. The locations of the SfiI (A) and SfiI (B) sites are shown as (A) and (B), respectively. Following ligation to seal the cohesive ends (in the middle), the DNA is cleaved by SfiI to expose the SfiI (A$^+$) and SfiI (B$^-$) sticky ends of the vector molecules. The small stuffer fragment is removed to prepare the vector arms shown at the bottom. The sequences of the single-stranded extensions are shown at both the 3'-ends of the cDNA and vector arms. Panel (C), formation of the λ concatemers containing cDNA inserts. The cDNA fragment shown at the left side are prepared to give the SfiI(A$^-$) and SfiI(B$^+$) sticky ends to the molecule by the procedure described in FIG. 3. When the fragments are ligated with the prepared vector arms, alternating concatemers consisting of the cDNA inserts and vector arms in the defined orientation are produced automatically due to the base-pairing specificity as shown in the middle. In vitro packaging extracts cut out the DNA segments hemmed by the two cos sites from the concatemer to form the active λ phage particles as shown at the bottom.
Figure 2B:
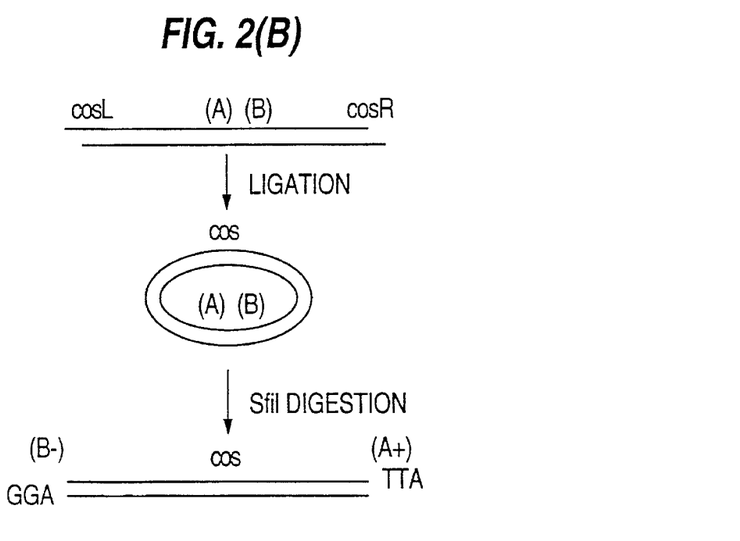
Figure 2C:
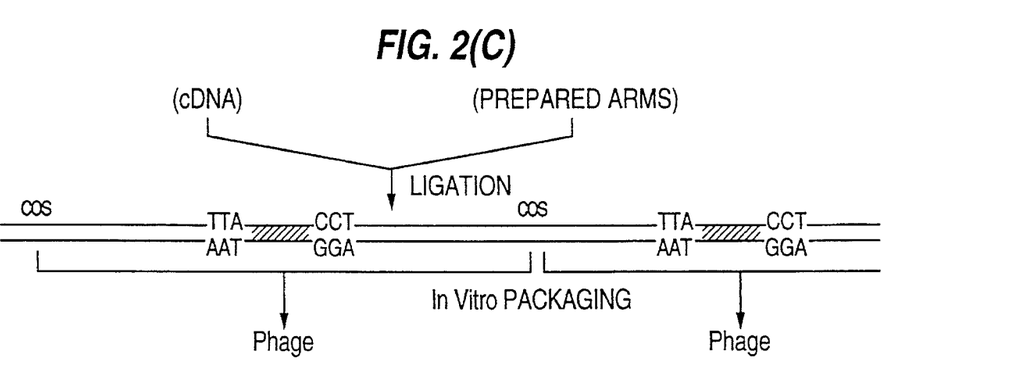

The reason why these self-ligation products and dimers are made, as noted above, is that majority of restriction enzymes in common usage recognize sequences of dyad symmetry. The two sticky ends ($S^+$ and $S^-$) created with an enzyme contain the same single-stranded extensions, and all combinations of the ends including $S^+$ and $S^+$ can be ligated. However, certain restriction enzymes cleave the non-symmetrical site (A), yielding two different sticky ends ($A^+$ and $A^+$. In this case, only $A^+$ and $A^-$ ends can be ligated (see FIG. 2). When a vector DNA containing two different sites (A and B) with this feature is cleaved by restriction enzymes of this kind, the stuffer fragment hemmed by the sites is removed, and ligation is performed with inserts having sticky ends complementary to those of the vector, theoretically all of the clones obtained contain single inserts in the defined orientation.

In a principal embodiment of this aspect of the invention, the restriction enzyme SfiI was chosen to cleave both the A and B sites, because SfiI is an infrequent cutter and leaves a non-symmetrical 3' extension of three nucleotides (FIG. 2A). Since the central 5 bases in the recognition site can be any sequence, two SfiI sites (A and B) were designed and introduced into the vectors (FIGS. 1 and 2B). The cDNA fragments to be inserted into the vectors were oriented by the use of oligo(dT) primers having attached the sequence of the SfiI (B) site.

Figure 3:
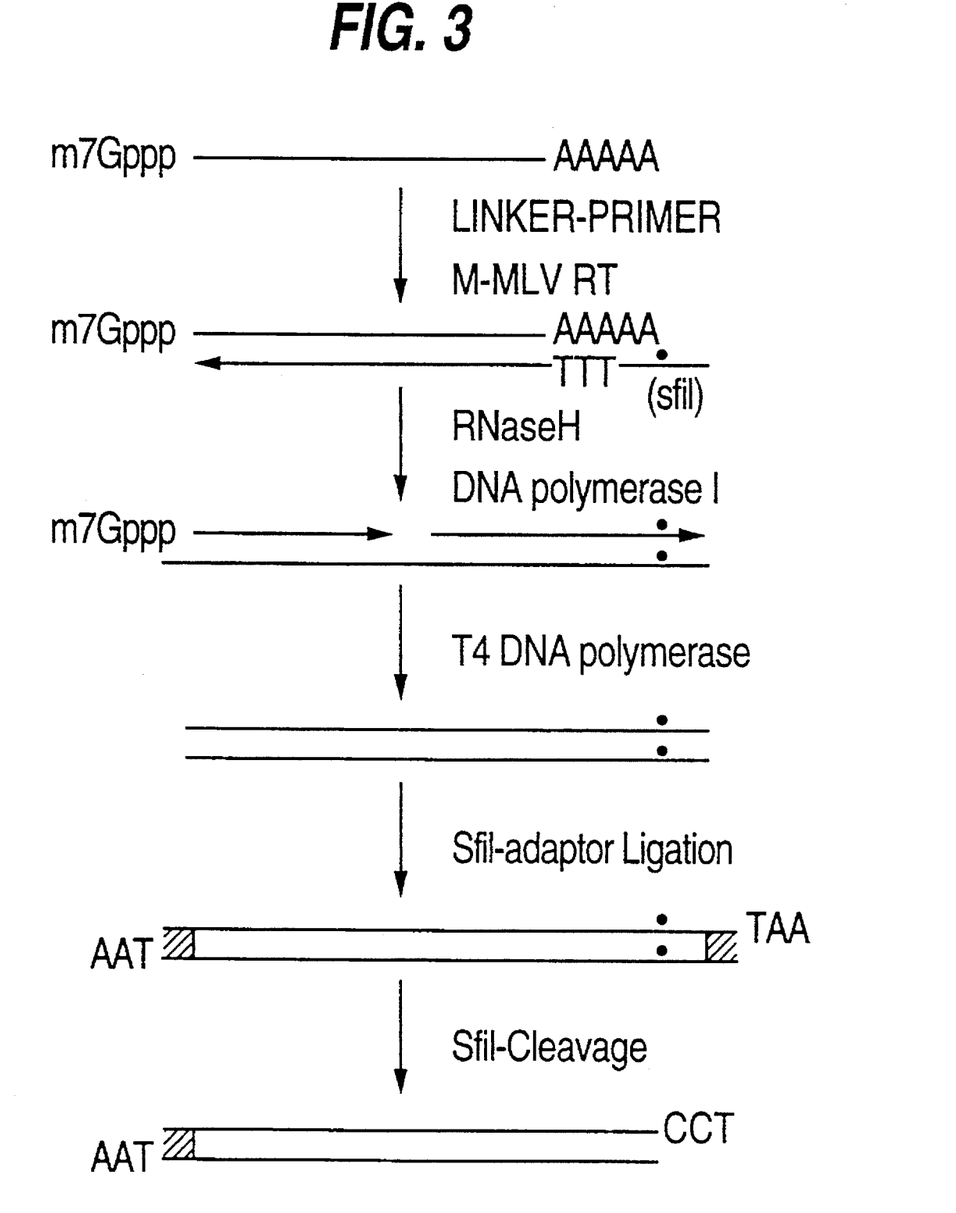

The steps for cDNA synthesis are schematically shown in FIG. 3. During the first strand synthesis reactions, the single-stranded linker-primer is repaired so as to be double-stranded. After cDNA molecules are blunt-ended, an adaptor, designated SfiI adaptor, having the 3' extension which fits to the SfiI (A$^+$) end, is ligated. After cleavage by SfiI, the resulting cDNA molecules have different 3' extensions which fit on the vector ends to achieve directional cloning (FIG. 2C).

Thus, regardless of the sequences of the three-base single-stranded sticky ends, inversion of one SfiI end sequence can never produce a self-complementary sequence. Accordingly, regardless of the sequence of the five arbitrary internal base pairs within any SfiI cleavage site, the polarity of the complementarity of the sticky ends will always be maintained. Thus, such inherently non-symmetrical sticky ends, as well as non-symmetrical variants of recognition sequences for which some forms can have dyad symmetry, as described above (e.g., BstXI), are also useful for practicing the automatic directional cloning method of the present invention, for efficient ligation of DNA fragments in a predirected order. Screenings of cDNA libraries constructed by this method, as described below, demonstrated that cDNAs of up to 6.4 kilobase pairs containing complete coding sequences could be isolated at high efficiency. Thus, this cloning system is particularly useful for the isolation of cDNAs of relatively long transcripts present even at low abundance in cells.

The present invention further relates to DNA of a genetic cloning vector comprising at least one replicon; and a site for inserting DNA segments to be cloned that includes at least two nonidentical restriction enzyme recognition sequences that are non-symmetrical, in which the non-symmetrical restriction enzyme recognition sequences have been cleaved by one or more enzymes that can cleave them, so that the DNA is ready for use in cloning DNA segments having matching sticky ends.

Finally, the present invention also relates to a reagent kit comprising cleaved vector DNA, ready for use in cloning, as described above, and further including a linker-primer having a single-stranded end that is complementary to one single-stranded end of the cleaved vector DNA; and an adaptor which after cleavage by a suitable restriction enzyme, has a single-stranded end that is complementary to the other single-stranded end of the cleaved vector DNA. One skilled in the art of genetic engineering would appreciate that such a kit might advantageously also include appropriate quantities of enzymes, buffers and other reagents needed for the practice of the automatic directional cloning method according to the teachings of the present invention.

The present invention may be understood more readily by reference to the following detailed description of specific embodiments and the Examples and Figures included therein.

BRIEF DESCRIPTION OF THE DRAWINGS

FIG. 1A and FIG. 1B. Structures of the vectors. Panel (A), λpCEV9 and panel (B), λpCEV15. Each vector contains a plasmid DNA within the λ DNA. An expanded map of the plasmid portion is shown with derivation of the DNA segments and the location of several restriction sites including the multiple cloning site (MCS). Arrows show the locations of the promoters and the direction of transcription.

FIG. 3. Schematic view of the cDNA synthesis. An mRNA molecule is shown at the top with the cap structure (m$^7$Gppp) and the poly(A) stretch (AAAAA) at the 5'- and 3'- ends, respectively. The linker-primer is the single-stranded oligonucleotide which contains the oligo(dT) at the 3' half, and the SfiI(B) site (shown by an asterisk) at the 5' half. The first strand is synthesized by Moloney murine leukemia virus reverse transcriptase (M-MLV RT) from the linker-primer hybridized with the RNA molecule. The second strand is synthesized by DNA polymerase I from the nicks on the RNA moiety introduced by RNase H. The linker-primer is converted to the double-stranded form in the first or second strand synthesis step. T4 DNA polymerase treatment makes double-stranded any single-stranded extensions remaining on the synthesized cDNA molecule. The SfiI adaptor ligation adds one 3' single-stranded extension, the SfiI (A$^-$) sticky end, to the cDNA molecule. Another 3' extension, the SfiI (B$^+$) sticky end, is exposed by SfiI cleavage of the SfiI (B) site on the repaired linker-primer portion of the cDNA molecule.

FIG. 4A, FIG. 4B, and FIG. 4C. Cloning of a model insert into pCEV15 using the ADC method. Panel (A), restriction map of pCEV15-RAS. The plasmid was constructed by cloning a 0.7 kbp fragment containing the mouse H-ras (v-bas) coding sequence (Reddy et al., 1985) into the EcoRI site of pCEV15. The open thick arc and closed thin arc represent the H-ras insert and vector, respectively. Panel (B), analysis of ligation products. pCEV15-RAS DNA was digested with SfiI, and vector (4.2 kb) as well as insert (0.7 kb) fragments were purified from the gel. Similarly, EcoRI/ApaI fragments were prepared as controls. The vector and/or H-ras insert SfiI fragments (left half) or EcoRI/ApaI fragments (right half) were incubated in kinase ligase buffer (see below) with or without T4 DNA ligase as indicated. The ligation products were analyzed by agarose gel electrophoresis. Sizes of the fragments are shown in kb. Panel (C), HindIII digestion of pCEV15 and its derivatives. (lane a) pCEV15; (lane b) pCEV15-RAS; (lane c) pCEV15 containing the H-ras insert in opposite orientation; (lane d) a marker (1-kb ladder; Bethesda Research Laboratories); and (other lanes) Plasmid DNAs isolated from 20 individual kanamycin-resistant colonies obtained by transformation of DH5a with the vector ligated to H-ras insert SfiI fragments.

DESCRIPTION OF SPECIFIC EMBODIMENTS

In one aspect, the present invention relates to a vector having nonidentical non-symmetrical restriction enzyme recognition site sequences, as described above, also including regulatory elements located such that the sequences of an inserted DNA segment are transcribed, where the regulatory elements are at least partly of eukaryotic origin. A principal embodiment of this aspect of the present invention is exemplified by two λ-plasmid composite vectors, λpCEV15 and λpCEV9, the structures of which are depicted in FIG. 1 and described further below, in Example 1.

Figure 4A:
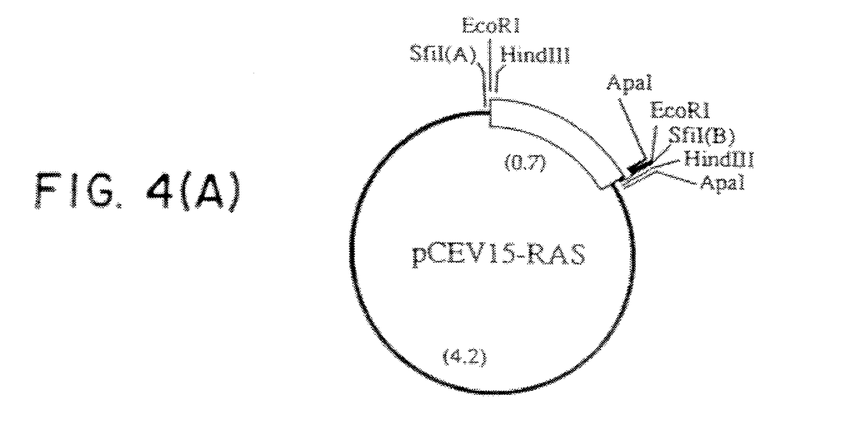

To examine the performance of the ADC method, a model H-ras insert was prepared so as to have SfiI(A$^-$) and SfiI(B$^+$) ends (FIG. 4A) and ligated with the pCEV15 SfiI fragment. To show the difference between the ADC method and the "forced" cloning method using two different restriction enzymes, a similar H-ras fragment with EcoRI and ApaI ends was prepared (FIG. 4A) and ligated with the pCEV15 EcoRI/ApaI fragment. To measure the efficiency of cDNA cloning using a natural template, 2.5 mg of a poly(A)+RNA preparation was denatured by heating and used to synthesize cDNA from a linker-primer. The results of all these experiments, described in Example 2, below, illustrate the remarkable efficiency of cloning of model inserts using this novel method of the present invention.

To assess the performance of the cDNA cloning method, cDNA was synthesized using poly(A)$^{30}$ RNA extracted from M426 human embryonic lung fibroblast cells under the conditions described in Example 2, below. cDNA molecules larger than 1 kb were selected by low melting point agarose gel electrophoresis, and two aliquots were used to clone into λpCEV9 and λpCEV15. The average size of the cDNA inserts was 2.0 kb in the λpCEV9 library (6×10$^6$ independent clones) and 2.2 kb in the λpCEV15 library (1×10$^7$ independent clones).

Figure 5A:
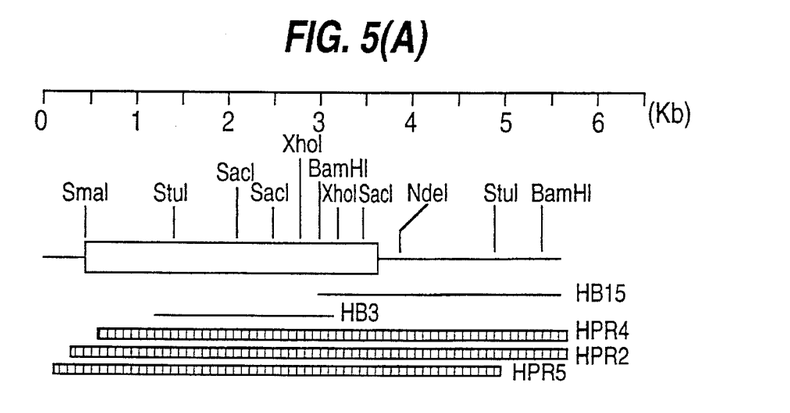
FIG. 5A, FIG. 5B, FIG. 5C and FIG. 5D. PDGF receptor clones isolated from the λpCEV9-M426 cDNA library. Panels (A) and (B), cDNA clones encoding for β and α PDGF receptors, respectively. The structure of each PDGF receptor cDNA is schematically shown with restriction sites. Open boxes represent coding sequences, while non-coding sequences are shown by bars. The clones shown by thick lines were isolated from the M426 cDNA library. The thin lines represent clones isolated from other libraries as described (Matsui, T., et al., 1989, Science 243, 800–804): HB15, HB3, and HB6 were derived from the human brain stem cell cDNA library in λgt11 (provided by R. Lazzarini; Matsui et al., 1989, supra); HF1 from the Okayama-Berg human fibroblast cDNA library (Okayama and Berg, 1982); and EF17 from a randomly-primed M426 cDNA library in λgt11 (Matsui et al., 1989, supra). Panels (C) and (D), nucleotide sequences of 5'-untranslated regions of β and α PDGF receptor clones HPR5 and TR4, respectively. Sequencing was performed by the chain termination method (Sanger et al., 1977, Proc. Natl. Acad. Sci. USA 74, 5463–5467). The initiation codons are underlined.
Figure 5B:
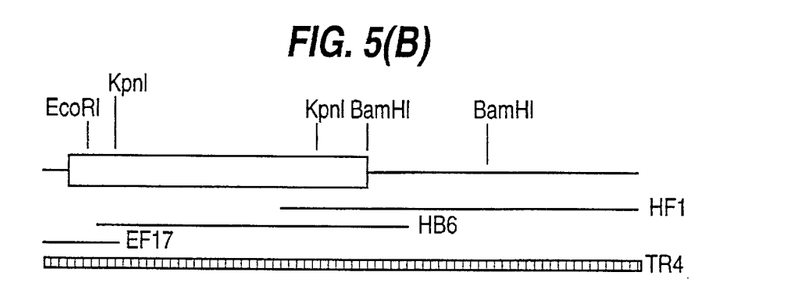
Figure 5C:
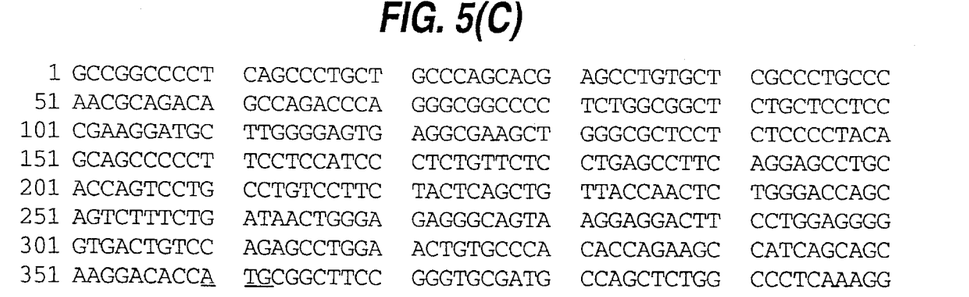
Figure 5D:
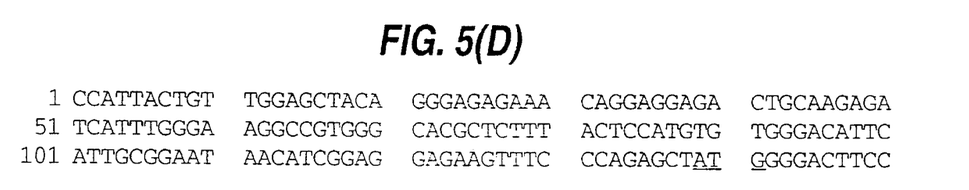

To characterize the M426 cDNA library in λpCEV9 further, it was screened for the human β PDGF receptor cDNA. Before this cDNA library was constructed, clones isolated (HB3 and HB15) by screening several other libraries did not contain the entire coding sequence (FIG. 5A). When a part (9×10$^5$ pfu) of the M426 cDNA library was screened for the human β PDGF receptor, six clones were isolated. Of these, three contained inserts of approximately 5 kb. Sequence analysis showed that two (HPR2 and HPR5) contained the entire coding sequence (FIG. 5A). Recently, Matsui et al., 1989, supra) have identified the cDNA of a novel PDGF receptor, designated the α PDGF receptor by isolation of overlapping cDNA clones (HF1, HB6 and EF17 in FIG. 5B). Re-probing of filters from M426 cDNA library for the human a PDGF receptor resulted in the isolation of 93 clones. Of 7 clones analyzed, 5 including TR4 contained inserts of 6.4 kb, which corresponded to the size of the message (FIG. 5B). As shown in FIGS. 5C and 5D, sequence analysis of α and β receptor cDNAs isolated from the M426 library revealed 5'- untranslated sequences followed by initiation codons for the complete coding sequence of each gene. These results indicated that the cDNA cloning system described here is suitable for isolation of relatively long cDNAs.

This method has been used for more than one year in the laboratory of these inventors, without public disclosure, to construct several cDNA libraries. Screening of the libraries for growth factors and receptors has been performed, and in most cases cDNA clones containing the entire coding sequence have been obtained as single clones. For example, a number of cDNA clones encoding keratinocyte growth factor have been isolated from the λpCEV9-M426 cDNA library using oligonucleotide probes. Screening of an MCF7 cDNA library in λpCEV9 constructed by the ADC method for a novel erbB-related gene resulted in the isolation of cDNA clones of 5 kb with high frequency as well. All of these findings indicate that the ADC method using αpCEV vectors makes it possible to clone relatively long cDNAs very efficiently.

From the present data, the following conclusions may be drawn:

(1) The ADC procedure resulted in very high cloning efficiency (10$^7$–10$^8$ clones/μg of mRNA).
(2) Usually backgrounds of libraries constructed by this method are very low. When the vector arms are prepared carefully, almost all of the clones contain cDNA inserts.
(3) cDNAs are inserted into the vectors in a directed orientation and as single inserts, making analysis of cDNA inserts simple and straightforward.
(4) The vectors can accommodate longer inserts than other λ vectors without sacrificing cloning efficiency, making possible to clone relatively long cDNA fragments.
(5) Plasmids carrying cDNA inserts can be released from λ genomes by NotI cleavage. This feature facilitates the structural analysis of cDNA clones, permits the generation of size-selected plasmid sub-libraries, and makes it possible to recover the cDNA clones by plasmid rescue from eukaryotic cells.

EXAMPLE 1

Construction of λpCEV15 and λpCEV9.

The following materials and methods were used in this and the subsequent examples, as needed.

Restriction enzymes, DNA polymerases, T4 DNA ligase, and T4 polynucleotide kinase were purchased from New England BioLabs, Bethesda Research Laboratories, and Boehringer Mannheim. M-MLV reverse transcriptase and RNaseH were from Bethesda Research Laboratories. Bacterial strain LE392; F⁻, hsdR511(rk⁻mk⁻) supE44 supF58 lacY1 or D (lacIZY)6 galK2 galT22 metB1 trpR55 was used as a host of λ. DH5α (Bethesda Research Laboratories) was used for bacterial transformation. NZY broth (10 g NZ amine, 5 g NaCl, 5 g Yeast extract in 1 l, pH 7.5) was used to grow bacterial strains. M426 is a human lung embryonic fibroblast cell line (Aaronson and Todaro, 1968, J. Virology 36, 254–261). Oligonucleotides were synthesized by a Beckman System 1 DNA Synthesizer and purified by high performance liquid chromatography. Oligonucleotides utilized had the following sequences.

1:GATCCGTCGACGGCCATTATGGCCAGAATTCTGGGCCCG,

2:TCGACGGGCCCAGAATTCTGGCCATAATGGCCGTCGACG,

3:AATTCAGGCCGCCTCGGCCAAGCTTAGATCTGGGCCCG,

4:TCGACGGGCCCAGATCTAAGCTTGGCCGAGGCGGCCTG,

5:TGGATGGATGG,

6:CCATCCATCCATAA,

7 and #8:GGACAGGCCGAGGCGGCC(T)n, where n=20 or 40 in the case of #7 and #8, respectively.

Plasmid DNA was prepared by the "selective precipitation procedure" which is a modification of the alkaline lysis method (Birnboim and Doly, 1979, Nucleic Acids Res. 7, 1513–1523). This technique makes it possible to prepare sufficient pure plasmid DNAs to analyze and alter structures, without a requirement for lysozyme treatment, phenol extraction or repeated ethanol precipitations. Cells collected from a 10 ml culture were resuspended into 0.2 ml of TEG (25 mM Tris-HCl pH 8.0/10 mM EDTA/50 mM glucose). After transfer to a microcentrifuge tube, 0.2 ml each of 2% sodium dodecyl sulfate and 0.4M NaOH was added, mixed, and incubated at room temperature for 5 min. After the addition of 0.2 ml of 3M ammonium acetate (pH 4.8), incubation at 0° C. for 10 min, and centrifugation for 15 min in a microcentrifuge, the supernatant was transferred to a fresh tube containing 0.2 ml of 2M Tris-HCl (pH 8.9) and 2 ml of 2 mg/ml RNase A. Following incubation at 37° C. for 30 min and centrifugation, the supernatant was transferred to a new tube containing 0.6 ml cold isopropanol. The tube was inverted several times and incubated at room temperature for 10 min. DNA was collected by centrifugation and then washed with 75% ethanol. The pellet was dried by incubation at 37° C. for 5 min and resuspended into 50 ml of 10 mM Tris-HCl (pH 8.0), 1 mM EDTA.

The λ DNAs prepared as follows were used to modify the structure, analyze cDNA clones in λpCEV vectors and then to rescue the plasmid part. Host cells grown in 10 ml of NZY medium containing 2 mM MgCl₂ were suspended into the same volume of SM buffer (50 mM Tris-HCl, pH 7.5/8 mM MgSO₄/100 mM NaCl/0.01% gelatin). A single plaque picked by a pasteur pipet was incubated with 0.1 ml of the host cell suspension at 37° C. for 30 min. Ten ml of pre-warmed NZY broth containing 2 mM MgCl₂ was added and shaken at 37° C. for 6 h. This procedure allows single-step production of high-titer lysates. Phage particles were precipitated and DNAs prepared as described by Arber et al, 1983 [In Hendrix, R. W., Roberts, J. W., Stahl, F. W. and Weisberg, R. A. (Eds.), Lambda II. Cold Spring Harbor Laboratory, Cold Spring Harbor, N.Y., 1983, pp. 433–466], with several modifications. A few drops of chloroform were added to the lysate, mixed and debris was removed by centrifugation. After the chloroform remaining in the lysate was removed by incubation at 37° C. 50 μl each of DNase I (1 mg/ml) and RNase A (1 mg/ml) were added, and incubated at 37° C. for 1 h. Phage particles were precipitated by the addition of 5 ml of 30%PEG/3M NaCl/10 mM MgCl₂ followed by incubation on ice for 1 h. Phage particles were collected by centrifugation at 3,000 rpm for 30 min., and the pellet was resuspended in 0.5 ml of SM. The suspension was transferred to a fresh microcentrifuge tube containing 20 μl of proteinase K (20 mg/ml). After incubation at 37° C. for 15 min, 50 μl of 100 mM Tris-HCl (pH8.0) /100 mM EDTA/ 1% sodium dodecylsulfate was added and the tube was incubated at 65° C. for 30 min. The released DNA was extracted by phenol/chloroform and then by chloroform. DNA was precipitated by 0.6 volume of isopropanol with 0.3 volume of 7.5M ammonium acetate, washed with 75% ethanol and dried. The pellet was dissolved in 10 mM Tris-HCl (pH 8.0), 1 mM EDTA, 0.1 mg/ml of RNase A and incubated at 37° C. for 30 min to digest ribosomal RNAs.

Plasmid DNAs prepared by the selective precipitation method were directly used to modify the structures, by restriction enzyme digestions, repair reactions, and/or ligation with synthetic linkers. DNA fragments were separated on agarose gels and then purified using GENECLEAN (BIO 101 Inc.).

Insertion of oligonucleotides was performed as follows. The two strands of non-phosphorylated oligonucleotides were annealed and ligated with plasmid DNA which has been digested with suitable restriction enzymes. One strand of the oligonucleotides which was not ligated (due to the 5'-OH structure) was removed by heating and then separated by agarose gel electrophoresis. The purified fragments were phosphorylated and then ligated.

Plasmid pCEV9 was constructed as follows. A retroviral vector pDOL⁻ (Korman et al., 1987, Proc. Natl. Acad. Sci. USA 84, 2150–2154) was cleaved by XbaI and recircularized to remove the polyoma segment. The ClaI site was converted to a NotI site by linker insertion, and the EcoRI site was removed by repair ligation. A synthetic MCS linker consisting of oligonucleotides #1 and #2 (see Example 1, below) was inserted between the SalI and BamHI sites, and the BclI/BamHI fragment of SV40 DNA (Bethesda Research Laboratories) containing its polyadenylation signal was inserted at the XhoI site. These manipulations produced pCEV9.

λgt11 DNA (Young and Davis, 1983, Proc. Natl. Acad. Sci. USA 80, 1194–1198) was ligated and then cleaved by EcoRI and XbaI. The ends were repaired and NotI-linkered, and then pCEV9 DNA linearized by NotI was cloned into the λ DNA to produce λpCEV9.

pCEV15 was constructed by modifying pCEV8, which is a parental plasmid of pCEV9 and lacks the MCS linker. A tac promoter fragment (Pharmacia) and XhoI linker were inserted in the SalI site. SfiI (B), HindIII, and BglII sites were removed successively by restriction enzyme digestion, polymerase treatment, and subsequent ligation reaction. Removal of the SfiI site (on the SV40 replication origin) did not impair the SV40 early promoter activity. The MCS linker was inserted between the BamHI and SalI sites, and SfiI (B), HindIII, and BglII sites were introduced again by insertion of the MCS-2 linker (oligonucleotides #3 and #4, below) between the EcoRI and ApaI sites. The resulting plasmid pCEV15 was cloned in a new λ vector constructed as follows. The segment spanning from the XhoI site to the right cos end of λpCEV9 was replaced by the corresponding fragment of λcharon28 (Rimm et al., 1980, Gene 12, 301–309), to introduce the cI deletion (KH54) and remove three HindIII sites. The resulting phage λpCEV9c DNA was ligated, cleaved by HindIII, and then repaired. A NotI linker was ligated to the repaired HindIII ends and the DNA was cleaved by NotI. The λ arms were purified and ligated with NotI-digested pCEV15 DNA, to produce λpCEV15.

EXAMPLE 2

Efficiency of cloning and orientation of model inserts.

Preparation of λ arms and the SfiI adaptor for all cloning experiments was performed as follows. λ DNA was ligated to seal cohesive ends and then cleaved sequentially by SfiI and EcoRI. After phenol/chloroform extraction, λpCEV9 arms were purified by centrifugation through a 5–20% potassium acetate gradient (Maniatis et al., 1982). μpCEV15 arms were purified passage through a Sephadex G-50 spin column (Boehringer Mannheim Biochem.).

The SfiI adaptor was prepared as follows. About 1 nmol of oligonucleotides #5 and #6 were separately phosphorylated by T4 polynucleotide kinase, mixed, heated at 80° C. for 5 min and then slowly cooled to 4° C.

RNA for making cDNAs was extracted and Poly (A)+ RNA selected as described by Okayama et al. (1987). cDNA was synthesized essentially according to D'Alessio et al. (1987) with some modifications. About 2.5 mg of poly(A)+ RNA in 10 ml of $H_2O$ was mixed with 0.5 ml of 100 mM methylmercuric hydroxide (MeHg), and incubated at room temperature for 5 min, followed by addition of 0.5 ml of 1.4M b-mercaptoethanol. After 5 min, 1.2 ml of RNasin (40 units/ml; Promega Biotech.), 17.8 ml of $H_2O$, 10 ml of 5× FS buffer (250 mM Tris-HCl, pH 8.3/375 mM KCl/15 mM $MgCl_2$/100 mM dithiothreitol), 2.5 ml of dNTP mixture (10 mM each of dGTP, dATP, dTTP and dCTP), 5 ml of linker-primer (oligonucleotide #8; 1 mg/ml) and 2.5 ml of M-MLV reverse transcriptase (200 units/ml) were sequentially added, mixed, and incubated at 37° C. for 1 h. The tube was chilled on ice and 290 ml of $H_2O$, 7.5 ml of dNTP mix (10 mM each of dGTP, dATP, dCTP, and TTP), 40 ml of 10× SS buffer (188 mM Tris-HCl, pH8.3/906 mM KCl/46 mM $MgCl_2$/38 mM DTT), 10 ml of DNA polymerase I (1.25 units/ml) and 1.8 ml of RNase H (0.25 units/ml) were added, mixed and incubated at 16° C. for 2 h. The reaction mixture was heated at 70° C. for 10 min, and 5 ml of T4 DNA polymerase (1 unit/ml) was added and incubated at 37° C. for 10 min. The reaction was terminated by the addition of 40 ml of 0.25M EDTA, and the mixture was extracted by phenol/chloroform twice followed by chloroform twice. cDNA was ethanol-precipitated from 2.5M ammonium acetate, washed, and then dried. The pellet was dissolved into 10 ml of $H_2O$ and then 4 ml of SfiI adaptor (0.8 mg/ml), 4 ml of 5× ligation buffer (500 mM Tris-HCl, pH7.6/100 mM $MgCl_2$/10 mM ATP/10 mM dithiothreitol/50% (w/v) polyethylene glycol-8000) and 2 ml of T4 DNA ligase (1 unit/ml) were mixed and incubated at 14° C. overnight. A 10 ml aliquot was then mixed with 1 ml of 10× SfiI buffer (100 mM Tris-HCl, pH 7.9/500 mM NaCl/100 mM $MgCl_2$/60 mM b-mercaptoethanol/1 mg/ml bovine serum albumin), 2 ml of SfiI (10 units/ml) and 7 ml of $H_2O$. Digestion was performed at 50° C. for 1 h. cDNA fragments were purified by low-melting point agarose gel electrophoresis or passing through a spun column (Maniatis et al., 1982) packed with Sepharose CL-4B (Pharmacia). An aliquot of the cDNA preparation was then mixed with λpCEV vector arms and ethanol-precipitated. DNA was dissolved in 8 ml of $H_2O$, and then 1 ml of 10× kinase-ligase buffer (660 mM Tris-HCl, pH7.5/100 mM MgCl/50 mM dithiothreitol, 500 mM ATP) and 1 ml of T4 DNA ligase (1 unit/ml) were added, mixed, and incubated at 14° C. overnight. In vitro packaging was performed using GigaPack Gold (StrataGene) as directed.

Figure 4B:
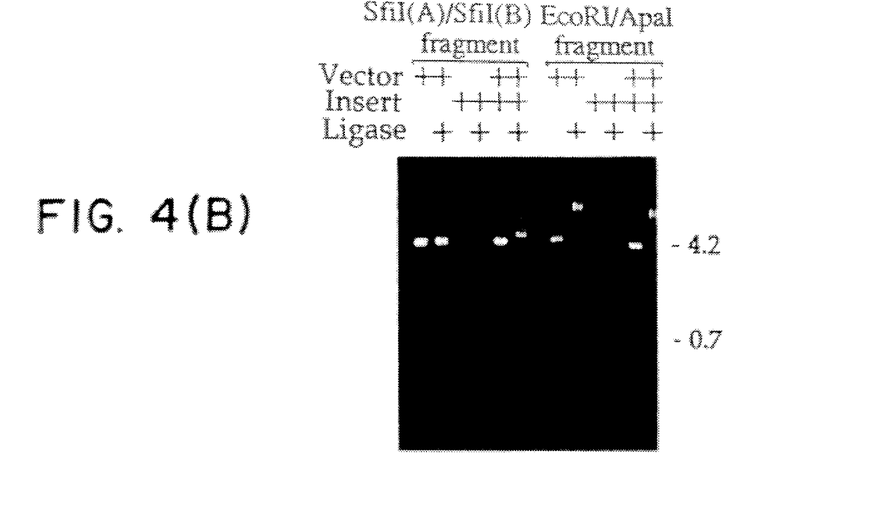
Figure 4C:
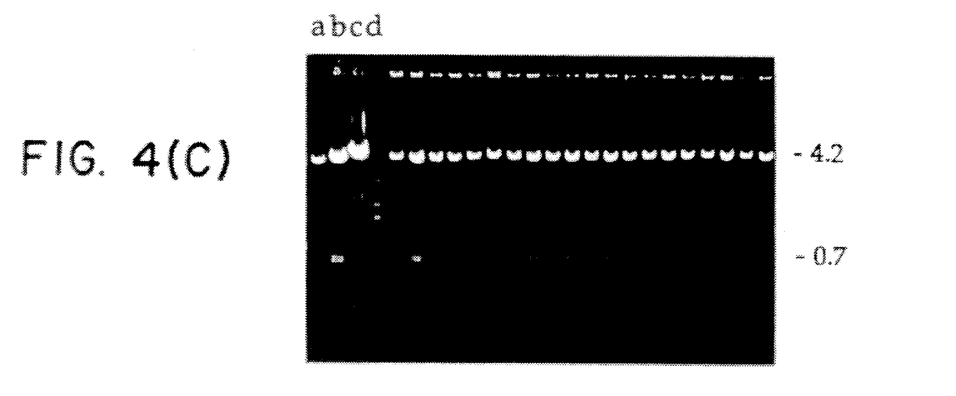

As shown in FIG. 4B, neither of the vector nor H-ras insert SfiI fragment was self-ligated, while self-ligation occurred when the EcoRI/ApaI fragments were used instead. In the ADC system, ligation occurred only when both the vector and insert fragments were present in the reaction mixture (FIG. 4B). To characterize the directional cloning capacity of the system, the H-ras insert and vector SfiI fragments were ligated, used to transform an E. coli strain DH5a, and 20 kanamycin-resistant colonies were analyzed. As shown in FIG. 4C, all plasmids contained single inserts in the expected orientation, indicating that the ADC method provides both directional cloning and positive selection for the presence of inserts. To further examine the performance of the ADC method using the λ system, model inserts prepared to have SfiI (A⁻) and SfiI (B⁺) ends were ligated with λpCEV9 arms (see FIG. 2C). As shown in Table I, pCEV9 arms alone did not produce active phages efficiently even when the ligation reaction was carried out, while presence of model inserts in

TABLE I

| Packaging efficiency of λpCEV9 DNA | |
|---|---|
| DNA | Titer[a] (pfu/μg λ arms) |
| λpCEV9 arms | $1 \times 10^3$ |
| λpCEV9 arms, ligated | $8 \times 10^3$ |
| λpCEV9 arms + Insert A[b], ligated | $8 \times 10^6$ |
| λpCEV9 arms + Insert B[c], ligated | $8 \times 10^6$ |

Footnotes for Table I:
[a]The reaction mixture contained 66 mM Tris-HCl (pH 7.5), 10 mM $MgCl_2$, 5 mM dithiothreitol, 50 mM ATP, and 0.1 μg/ml of DNA. Incubation was performed at 14° C. overnight, and the phage were produced by in vitro packaging and titered on LE392.
[b]A 2 kb DNA fragment having the SfiI(A⁻) and SfiI(B⁺) ends (see FIG. 2).
[c]A DNA fragment similar to the insert A, except that the SfiI(A⁻) end was created by ligation of the SfiI adaptor.

the ligation mixture increased the titer of active phages by three orders of magnitude. These results indicated that successful ligation and phage propagation depended on the presence of the model insert in the reaction mixture. All of these findings indicated that the cloning procedure results in low background and efficient directional cloning.

To measure the efficiency of cDNA cloning using a natural template, 2.5 mg of a poly(A)+ RNA preparation was denatured by heating used to synthesize cDNA from a linker-primer (oligonucleotide #7). The cDNA was blunt-ended, and the SfiI adaptor was ligated to both the ends. The molecules were cleaved partially by SfiI, and then cloned in λpCEV9. A total of $2.5 \times 10^8$ plaque forming units (pfu) was obtained, indicating that the method was extremely efficient.

Since SfiI is an infrequent cutter, almost all cDNA species in the libraries constructed by the ADC method should remain intact. Nonetheless, cDNAs containing SfiI sites might be excluded from our cDNA libraries. To solve the problem, partial SfiI digestion is usually performed. An alternative strategy involves cDNA synthesis from a linker-primer containing the recognition site of another infrequent cutter MluI, in addition to the SfiI site. The cDNA preparation could then be divided into two parts, one cleaved by SfiI and the other by MluI. A short oligonucleotide ligated to the cDNAs could be utilized to convert the MluI end to an SfiI(B$^+$) end.

For purposes of completing the background description and present disclosure, each of the published articles, patents and patent applications heretofore identified in this specification are hereby incorporated by reference into the specification.

The foregoing invention has been described in some detail for purposes of clarity and understanding. It will also be obvious that various combinations in form and detail can be made without departing from the scope of the invention.

What is claimed is:

1. A directional cloning vector comprising
   at least one replicon; and
   a site for inserting DNA segments to be cloned, wherein said site is flanked by non-symmetrical restriction enzyme recognition sequences that are not identical to each other but that can be cleaved by the same restriction enzyme, such that the single-stranded ends formed by cleaving both of said restriction enzyme recognition sequences with said same restriction enzyme are neither complementary to each other nor self-complementary, thereby preventing the formation of dimer and self-circularized by-products during ligation.

2. A directional cloning vector according to claim 4, wherein said same restriction enzyme is selected from the group consisting of BstXI and SfiI.

3. A directional cloning vector according to claim 1, wherein said vector is a phage-plasmid vector.

4. A directional cloning vector according to claim 1, wherein said replicon comprises a form of bacteriophage λ.

5. A directional cloning vector according to claim 4, further comprising regulatory elements that are located in relation to said site for inserting DNA segments such that, when a DNA segment is inserted into said site to form a recombinant structure, at least a portion of the sequence of said DNA segment is transcribed when said recombinant structure is within a suitable host.

6. A directional cloning vector according to claim 5, wherein said regulatory elements comprise bacteriophage promoters.

7. A directional cloning vector according to claim 5, wherein said regulatory elements comprise eukaryotic promoter sequences.

8. A directional cloning vector according to claim 7, further comprising a selectable marker that is functional in eukaryotic cells.

9. A method for directionally cloning a cDNA copy of a messenger RNA, comprising the steps of:
   (i) annealing a linker-primer DNA segment with poly(A) mRNA, wherein said linker-primer DNA segment comprises a single-stranded oligonucleotide which comprises oligo(dt) at the 3' end, and a single-stranded extension at the 5' end with a sequence corresponding to a first non-symmetrical restriction enzyme recognition sequence;
   (ii) enzymatically synthesizing the first strand of said cDNA from the linker-primer that is annealed with said poly(A) mRNA;
   (iii) enzymatically synthesizing the second strand of said cDNA using said first strand as a template under conditions such that single-stranded extensions on the synthesized cDNA molecule are made double-stranded, whereby the cDNA is made blunt-ended;
   (iv) ligating onto said blunt-ended cDNA an adaptor DNA segment comprising a second non-symmetrical restriction enzyme recognition sequence that is not identical to said first non-symmetrical restriction enzyme recognition sequence but that can be cleaved by the same restriction enzyme, such that the single stranded ends formed by cleaving both said restriction enzyme recognition sequences with said same restriction enzyme are neither complementary to each other nor self-complementary, thereby preventing the formation of dimer and self-circularized by-products during ligation;
   (v) exposing said cDNA resulting from ligation with said adaptor said same restriction enzyme under conditions such that both of said restriction enzyme recognition sequences are cleaved, resulting in said cDNA having two single-stranded ends that are not complementary;
   (vi) ligating said cDNA resulting from cleavage with said same restriction enzyme to a directional cloning vector to form a recombinant DNA structure, said vector comprising at least one replicon and a site for inserting DNA segments to be cloned, wherein said site for inserting is flanked by non-symmetrical restriction enzyme recognition sequences that are not identical to each other but that have been cleaved by said same restriction enzyme, such that the single-stranded ends formed by cleaving both said restriction enzyme recognition sequences with said same restriction enzyme are neither complementary to each other nor self-complementary, thereby preventing the formation of dimer and self-circularized by-products during ligation and wherein during said ligating said cDNA is inserted into said site for inserting;
   (vii) transforming a suitable host cell with said recombinant DNA structure; and
   (viii) identifying a clone of host cells that contains a recombinant DNA structure including said cDNA.

10. A method according to claim 9, wherein said same restriction enzyme is selected from the group consisting of BstXI and SfiI.

11. A reagent kit comprising
    (i) a directional cloning vector comprising
        at least one replicon; and
        a site for inserting DNA segments to be cloned, wherein said site is flanked by non-symmetrical restriction enzyme recognition sequences that are not identical to each other but that can be cleaved by the same restriction enzyme, such that the single stranded ends formed by cleaving both said restriction enzyme recognition sequences with said same restriction enzyme are neither complementary to each other nor self-complementary, thereby preventing the formation of dimer and self-circularized by-products during ligation;
    (ii) an adaptor having a single-stranded end that is complementary to one single-stranded end of said directional cloning vector; and
    (iii) a linker-primer which after cleavage by a suitable restriction enzyme following second strand cDNA synthesis has a single-stranded end that is complementary to the other single-stranded end of said directional cloning vector.

12. A reagent kit according to claim 11, wherein said same restriction enzyme is selected from the group consisting of BstXI and SfiI.

* * * * *